(12) United States Patent
Sekiguchi et al.

(10) Patent No.: US 9,797,609 B2
(45) Date of Patent: Oct. 24, 2017

(54) LOCAL CLEANED AIR SUPPLY DEVICE

(71) Applicant: NIKKA MICRON CO., LTD., Misato-shi, Saitama (JP)

(72) Inventors: Shigeo Sekiguchi, Misato (JP); Hiroyuki Shuto, Misato (JP)

(73) Assignee: NIKKA MICRON CO., LTD., Misato-Shi, Saitama (JP)

( * ) Notice: Subject to any disclaimer, the term of this patent is extended or adjusted under 35 U.S.C. 154(b) by 82 days.

(21) Appl. No.: 14/773,757

(22) PCT Filed: Apr. 5, 2013

(86) PCT No.: PCT/JP2013/060526
§ 371 (c)(1),
(2) Date: Sep. 9, 2015

(87) PCT Pub. No.: WO2014/162603
PCT Pub. Date: Oct. 9, 2014

(65) Prior Publication Data
US 2016/0018117 A1    Jan. 21, 2016

(51) Int. Cl.
| | |
|---|---|
| *B01D 46/42* | (2006.01) |
| *B01D 35/30* | (2006.01) |
| *B01D 39/16* | (2006.01) |
| *F24F 3/16* | (2006.01) |
| *A61B 90/13* | (2016.01) |
| *F24F 1/00* | (2011.01) |

(Continued)

(52) U.S. Cl.
CPC ........... *F24F 3/1607* (2013.01); *A61B 90/13* (2016.02); *A61B 90/40* (2016.02);
(Continued)

(58) Field of Classification Search
CPC ........ B01D 46/42; B01D 35/30; B01D 39/16; F24F 3/1607; F24F 2221/12; A61G 13/108
(Continued)

(56) References Cited

U.S. PATENT DOCUMENTS 3,724,172 A * 4/1973 Wood ............... A61G 10/02
128/205.26
4,963,134 A * 10/1990 Backscheider ..... A61M 1/0023
55/467
(Continued)

FOREIGN PATENT DOCUMENTS

JP     52152677 A     12/1977
JP     6091256 U      6/1985
(Continued)

OTHER PUBLICATIONS

International Search Report (ISR) dated May 21, 2013 issued in International Application No. PCT/JP2013/060526.

*Primary Examiner* — Jacob T Minskey
*Assistant Examiner* — Minh-Chau Pham
(74) *Attorney, Agent, or Firm* — Holtz, Holtz & Volek PC

(57) ABSTRACT

A local cleaned air supply device includes: a power supply unit, a control unit, and a freely rotatable cleaned air supply unit. The cleaned air supply unit, which includes a fan driven by driving electric power, and of which a height position, a swing angle in a left-right direction, and a tilting angle can be freely adjusted, is configured so that air drawn therein is cleaned by passing through a pre-filter and a main filter and is then discharged toward a front side thereof from an air discharge opening. The cleaned air supply unit also includes a sighting unit that visualizes a range in which high cleanliness is guaranteed in a space on the front side of the cleaned air supply unit. The sighting unit includes a plurality of laser emitting units that output laser beams, to surround the range, toward a front side of the air discharge opening.

19 Claims, 2 Drawing Sheets

(51) Int. Cl.
*A61B 90/40* (2016.01)
*A61B 90/50* (2016.01)

(52) U.S. Cl.
CPC ........ B01D 46/4254 (2013.01); F24F 3/1603 (2013.01); *A61B 90/50* (2016.02); *A61B 2090/401* (2016.02); *F24F 2001/0096* (2013.01); *F24F 2221/38* (2013.01)

(58) Field of Classification Search
USPC ... 55/356, 385.1, 385.2, 472, 473, 482, 501, 55/502, 504; 95/273; 128/132; 98/115 R, 115.4, 115.1, 33.1, 36; 422/122; 96/223
See application file for complete search history.

(56) References Cited

U.S. PATENT DOCUMENTS

| | | | | |
|---|---|---|---|---|
| 5,312,465 A | * | 5/1994 | Riutta | B01D 46/0049 454/230 |
| 6,099,607 A | * | 8/2000 | Haslebacher | F24F 3/1607 55/356 |
| 6,513,529 B1 | * | 2/2003 | Kamen | A61B 90/40 128/847 |
| 8,319,195 B2 | * | 11/2012 | Berry | A61L 2/08 204/660 |
| 2007/0263173 A1 | | 11/2007 | Reimer et al. | |
| 2011/0037947 A1 | | 2/2011 | Reimer et al. | |
| 2012/0024154 A1 | * | 2/2012 | Augustine | A47C 7/744 95/273 |
| 2012/0031271 A1 | * | 2/2012 | Haslebacher | B01D 46/10 95/273 |
| 2012/0132829 A1 | * | 5/2012 | Wang | B65G 49/067 250/454.11 |

FOREIGN PATENT DOCUMENTS

| | | |
|---|---|---|
| JP | 2000316962 A | 11/2000 |
| JP | 2006147482 A | 6/2006 |
| JP | 2006150327 A | 6/2006 |
| JP | 2008509428 A | 3/2008 |

* cited by examiner

LOCAL CLEANED AIR SUPPLY DEVICE

TECHNICAL FIELD

The present invention relates to a local cleaned air supply device capable of supplying highly clean air in a local interior area.

BACKGROUND ART

Products which require an extremely high clean environment during manufacturing like precision apparatuses including semiconductors and sterilizing medical apparatuses are manufactured in a clean room in which the entire interior space is highly cleaned. The application of a clean room or an air cleaner and the like for realizing the clean room is not limited to, for example, manufacturing facilities for precision apparatuses. For example, when such techniques are applied to medical fields (an operating room, a treatment room, or the like), the possibility of infection during the operation or treatment can be reduced remarkably.

However, when the air cleaner and the like are applied to an operating room or a treatment room in order to avoid infection, not the entire interior space thereof has to be created in a highly cleaned state but it is sufficient to create a highly clean space locally in a predetermined range around a target area (an affected area subject to an operation or a treatment target area). From this respect, a device (a local cleaned air supply device) capable of supplying cleaned air to a local specific range only rather than the entire interior space is known.

CITATION LIST

Patent Literature

Patent Literature 1: Japanese Patent Application Publication No. 2000-316962
Patent Literature 2: Japanese Patent Application Publication No. 2006-150327

SUMMARY OF INVENTION

Technical Problem

A local cleaned air supply device cleans air taken in from the interior with the aid of a HEPA filter or the like and then blows the cleaned air in a fixed direction to form a highly clean space in a limited interior area (a front area of an air discharge opening). When the local cleaned air supply device operates, a highly clean space and the other space are present in the interior space. However, it is naturally not possible to visually perceive the boundary between the two spaces. Thus, the following problems occur.

The space in front of the air discharge opening of the local cleaned air supply device, in which air flows strongly, can be considered to be a "highly clean space". However, dust or the like present around and near the boundary of the highly clean space may be drawn into the space, and the highly clean space may not be necessarily highly clean. Thus, the highly clean space is a limited area (within a certain range from the central line of the flow or air) closer to the inner side than the boundary of the flow of air.

When infection which can occur during the operation or treatment is to be prevented using a local cleaned air supply device, it is necessary to adjust the blowing direction of cleaned air so that a certain range around a target area such as an affected area is positioned inside a highly clean space formed by the local cleaned air supply device. However, as described above, since it is not possible to visually perceive the boundary between the highly clean space and the other space, the adjustment is complex and takes a lot of time. Further, it is difficult to check whether the blowing direction is suitable (whether the target area is positioned inside the highly clean space).

Naturally, such a problem does not occur if the air discharge opening can be disposed at a position very close to a target area. However, various apparatuses for operation or treatment are often disposed at the position very close to the target area, and the space for operation or treatment is required. Thus, the air discharge opening has to be disposed at a position distant from the target area. The operation of adjusting the blowing direction becomes difficult in proportion to the separation distance from the target area.

Moreover, after the adjustment operation is completed, the blowing direction may be changed contrary to the user's intention due to an external force or the like during continuation of operation or treatment and the target area may be positioned outside the highly clean space. In this case, since it is not possible to visually perceive the boundary of the highly clean space, the operation or treatment is continued without understanding such a situation.

Further, when the installed position of the air discharge opening cannot be secured within a range sufficiently close to a target area (the air discharge opening has to be installed at a distant position), it may be difficult to form the highly clean space near the target area. In this case, since it is not possible to visually perceive the boundary, it is not possible to check whether the target area is positioned inside the highly clean space.

The present invention has been made to solve the problems of the related art, and an object thereof is to provide a local cleaned air supply device capable of visually perceiving the range of a highly clean space, easily adjusting a blowing direction of cleaned air, and easily checking whether the blowing direction is suitable.

Solution to Problem

A local cleaned air supply device according to the present invention includes: a power supply unit; a control unit; and a cleaned air supply unit supported so as to freely rotate, wherein the cleaned air supply unit includes a fan driven by driving electric power supplied from the power supply unit, a pre-filter, and a main filter, and is configured so that air drawn therein is cleaned by passing through the pre-filter and the main filter and is then discharged toward a front side of the cleaned air supply unit from an air discharge opening and so that a height position, a swing angle in a left-right direction, and a tilting angle of the cleaned air supply unit can be freely adjusted, the cleaned air supply unit includes a sighting unit that visualizes a range in which high cleanliness is guaranteed in a space on the front side of the cleaned air supply unit, to which the cleaned air is supplied from the air discharge opening, and the sighting unit includes a plurality of laser emitting units that output laser beams toward a front side of the air discharge opening, and the laser beams are output to surround the range in which high cleanliness is guaranteed in the space in the front side of the cleaned air supply unit.

Preferably, the cleaned air supply unit is supported by, for example, a post via a freely articulated arm having a plurality of hinges and is configured to freely adjust a three-dimensional position thereof.

Preferably, the laser beams are output so as to pass through positions separated by a predetermined distance from a central line of the flow of the cleaned air discharged from the air discharge opening in parallel to the central line.

Preferably, an acceleration sensor is included in a casing of the cleaned air supply unit, and when a three-dimensional position, the swing angle in the left-right direction, or the tilting angle of the cleaned air supply unit is changed, the acceleration sensor detects the change, and laser beams, spot laser beams, and spot beams are automatically output for a predetermined period after the detection.

Preferably, a distance meter is disposed in the cleaned air supply unit so as to automatically measure the distance from the cleaned air supply unit to a target area, and when the distance exceeds a predetermined value, a warning is output to inform that high cleanliness is not guaranteed in the range visualized by the sighting unit.

Preferably, a threshold of the separation distance for determining whether or not to output the warning is set to an appropriate value automatically according to a set flow of the cleaned air discharged from the air discharge opening.

Advantageous Effects of Invention

According to the local cleaned air supply device of the present invention, the sighting unit visualizes the range of the highly clean space formed on the front side of the cleaned air supply unit by the cleaned air supplied from the air discharge opening and can easily visually perceive the boundary between the highly clean space and the other space. Thus, it is possible to easily adjust the blowing direction of the cleaned air and to check whether the blowing direction is suitable.

Moreover, the acceleration sensor is included in the casing of the cleaned air supply unit so that, when the three-dimensional position or the like of the cleaned air supply unit is changed, the acceleration sensor detects the change and laser beams or the like are output for a predetermined period after the detection. In this case, when the blowing direction is changed contrary to the user's intention during use, it is possible to immediately inform the user of the change. When the target area is positioned outside the highly clean space, it is possible to immediately adjust the discharging direction again.

Further, the distance meter is disposed in the cleaned air supply unit so that a warning is output to inform that the cleaned air supply unit is too far from the target area. In this case, since it is possible to check the separation distance (the distance from the target area to the air discharge opening) in which high cleanliness is guaranteed, it is possible to ideally obviate a problem that an operation or a treatment is conducted at a position deviated from the highly clean space.

DESCRIPTION OF EMBODIMENTS

Figure 1:
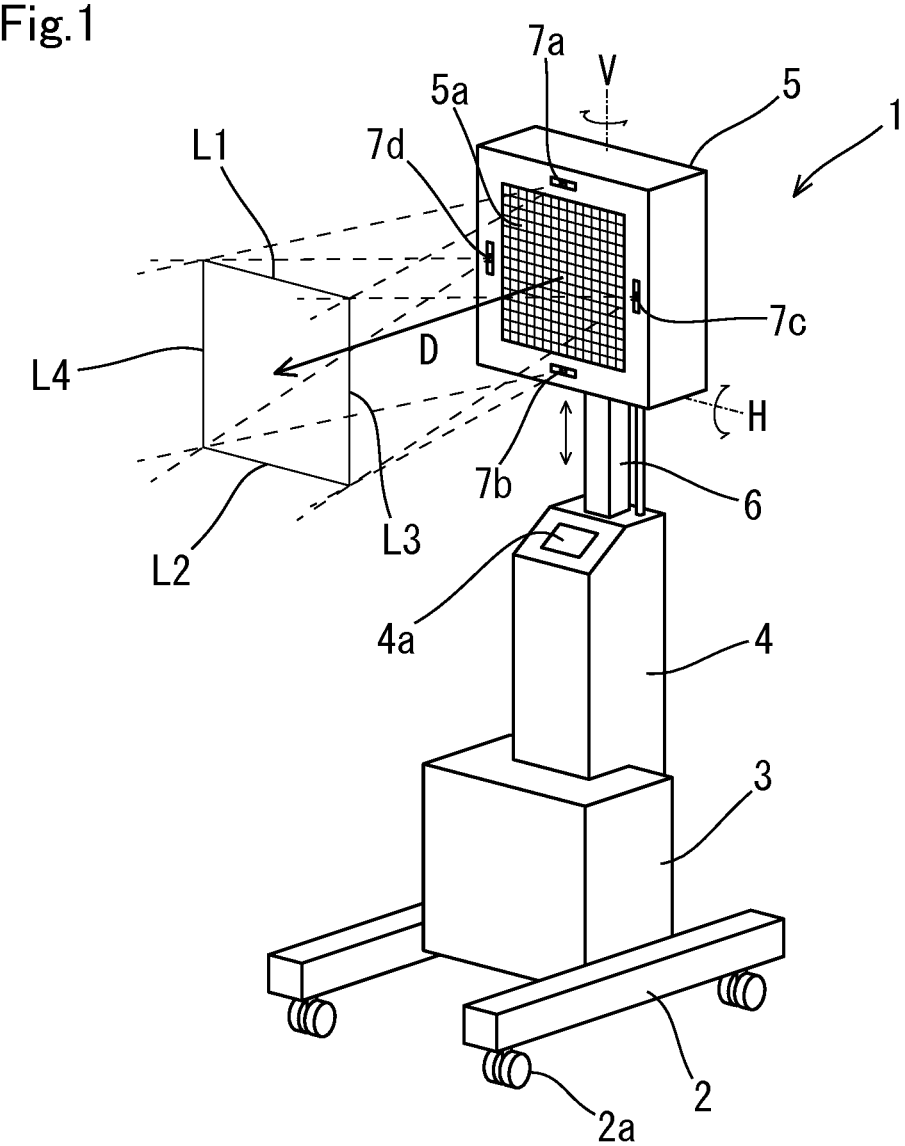
FIG. 1 is a perspective view of a local cleaned air supply device 1 according to a first embodiment of the present invention.

Hereinafter, embodiments (first and second embodiments) of a "local cleaned air supply device" according to the present invention will be described with reference to the accompanying drawings. FIG. 1 is a perspective view of a local cleaned air supply device 1 according to a first embodiment of the present invention. As illustrated in the drawing, the local cleaned air supply device 1 basically includes a base 2, a power supply unit 3 placed on the base 2, a control unit 4, and a cleaned air supply unit 5 supported above the control unit 4.

The base 2 has castors 2a attached to a lower end thereof so that the entire device can be moved easily. Moreover, by operating a stopper assembled to the castor 2a, the device can be easily put to an immovable state.

The power supply unit 3 supplies electric power to the control unit 4 and the cleaned air supply unit 5 and has a battery mounted thereon as well as a power cord (not shown in figures) for AC 100 V. Thus, the device can be used by connecting the power cord to a commercial power outlet and can be used without connecting to the power outlet by charging the battery in advance.

The cleaned air supply unit 5 includes a fan driven by driving electric power supplied from the power supply unit 3, a pre-filter formed of nonwoven fabric, and a main filter formed of a HEPA filter. Moreover, when the fan is driven, air is drawn from an air intake opening (not illustrated) formed in a back surface. The air drawn into the device is cleaned by passing through the pre-filter and the main filter and is then discharged toward a front side from an air discharge opening 5a formed in a front surface.

The cleaned air supply unit 5 is attached to an upper end of an elevatable post 6 so as to freely rotate about a vertical axis line V and a horizontal axis line H. A height position can be adjusted by moving the cleaned air supply unit 5 in an up-down direction in relation to the power supply unit 3 and the control unit 4. Moreover, a swing angle in a left-right direction and a tilting angle can be freely adjusted. Due to this, the direction in which cleaned air is supplied from the air discharge opening 5a can be set freely.

A sighting unit (a laser emitting unit 7) is disposed on a front surface (around or inside the air discharge opening 5a) of the cleaned air supply unit 5. This sighting unit visualizes the range of a highly clean space (more specifically, the range in which cleanliness of class 100 is guaranteed) formed on the front side of the cleaned air supply unit 5 by the cleaned air supplied from the air discharge opening 5a.

In the present embodiment, the sighting unit includes four laser emitting units 7 (7a to 7d). More specifically, as illustrated in FIG. 1, the laser emitting units 7a to 7d are disposed on upper, lower, and left and right sides of the air discharge opening 5a on the front side of the cleaned air supply unit 5, respectively. Horizontal laser beams (horizontal reference lines L1 and L2) are output toward the front side of the air discharge opening 5a from the laser emitting units 7a and 7b, respectively. Vertical laser beams (vertical reference lines L3 and L4) are output from the laser emitting units 7c and 7d, respectively.

These laser beams (reference lines L1 to L4) are output so as to pass through positions separated by a predetermined distance from a central line D of the flow of the cleaned air discharged from the air discharge opening 5a in parallel to the central line D to thereby surround a highly clean space of class 100 formed on the front side of the cleaned air supply unit 5 by the cleaned air supplied from the air discharge opening 5a.

Thus, when the local cleaned air supply device 1 is installed in an operation room to maintain a local space around an affected area of a patient in a highly clean state during an operation conducted on the patient, the height position, the swing angle in the left-right direction, and the tilting angle of the cleaned air supply unit 5 may be adjusted so that the affected area of the patient is surrounded by the laser beams (reference lines L1 to L4) output from the laser emitting units 7a to 7d.

In the present embodiment, an acceleration sensor is included in a casing of the cleaned air supply unit 5. When the height position, the swing angle in the left-right direction, or the tilting angle of the cleaned air supply unit 5 is changed, the acceleration sensor detects the change, and laser beams are automatically output from the laser emitting units 7a to 7d for a predetermined period (for example, 5 seconds) after the detection. Thus, when a user moves the cleaned air supply unit 5 slightly in order to perform alignment (adjustment of the height or orientation of the cleaned air supply unit 5 or adjustment of the blowing direction of cleaned air), laser beams are output so that the user can adjust the height or orientation of the cleaned air supply unit 5 with reference to the reference lines L1 to L4 emitted to a target area (an affected area or the like of a patient) or a surrounding portion thereof.

Moreover, even when the local cleaned air supply device 1 is moved or the orientation of the cleaned air supply unit 5 is changed contrary to the user's intention due to an external force, the acceleration sensor responds to the movement or the change and laser beams are output automatically from the laser emitting units 7a to 7d. Thus, the user can easily check whether the highly clean space of class 100 formed by the cleaned air discharged from the cleaned air supply unit 5 deviates from the target area (the affected area or the like of the patient).

The laser beams may be output manually from the laser emitting unit 7a to 7d when an operation panel 4a of the control unit 4 is operated.

Figure 2:
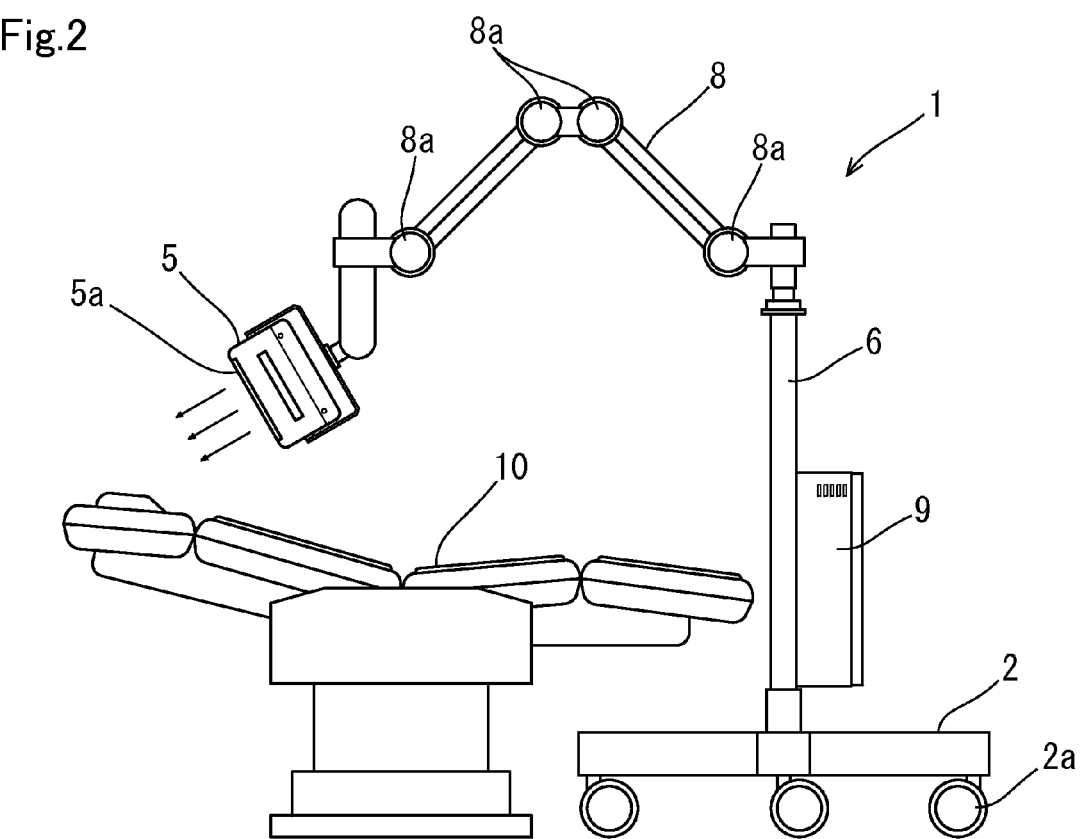
FIG. 2 is a side view of a local cleaned air supply device 1 according to a second embodiment of the present invention.

FIG. 2 is a side view of a local cleaned air supply device 1 according to a second embodiment of the present invention. In the present embodiment, a cleaned air supply unit 5 is supported on an upper end of a post 6 by a freely articulated arm 8 having a plurality of hinges 8a. Thus, the cleaned air supply unit 5 can be freely moved in an up-down direction, a left-right direction, and a front-rear direction from the position illustrated in FIG. 2. Moreover, a three-dimensional position of the cleaned air supply unit 5 can be freely adjusted within a movable range of the freely articulated arm 8. Further, a swing angle in the left-right direction and a tilting angle of the cleaned air supply unit 5 can be freely adjusted. Due to this, the direction in which cleaned air is supplied from an air discharge opening 5a can be set freely. Thus, for example, as illustrated in FIG. 2, the cleaned air supply unit 5 can be disposed above an operating table 10 at a position in which the cleaned air supply unit 5 does not interfere with various apparatuses for operation or treatment.

The local cleaned air supply device 1 of the present embodiment is approximately the same as that of the first embodiment except that the cleaned air supply unit 5 is supported by the freely articulated arm 8. That is, castors 2a with stoppers are attached to a lower end of a base 2. The power supply unit (in the present embodiment, the power supply unit is accommodated in a control box 9 together with a control unit) has a battery mounted thereon as well as a power cord. The cleaned air supply unit 5 includes a fan, a pre-filter (nonwoven fabric), and a main filter (HEPA filter) and discharges cleaned air toward a front side from an air discharge opening 5a formed in a front surface thereof.

Moreover, an acceleration sensor is included in the cleaned air supply unit 5. Further, a sighting unit (laser emitting units 7a to 7d) for visualizing the range of a highly clean space of class 100 formed on the front side of the cleaned air supply unit 5 by the cleaned air supplied from the air discharge opening 5a is disposed on the front surface of the cleaned air supply unit 5.

In the first and second embodiments, the laser emitting units 7a to 7d that output the horizontal reference lines L1 and L2 and the vertical reference lines L3 and L4 toward the front side of the air discharge opening 5a so as to surround the highly clean space of class 100 formed on the front side of the cleaned air supply unit 5 are used as the sighting unit. However, the laser emitting unit may be disposed at the center of the air discharge opening 5a so that an output spot laser beam is identical to the central line D of the flow of cleaned air discharged from the air discharge opening 5a, and a spot beam rather than a laser beam may be output from an LED (or other light sources).

In this case, the height position (or a three-dimensional position), the swing angle in the left-right direction, the tilting angle, and the like of the cleaned air supply unit 5 may be adjusted to realize alignment (adjustment of the blowing direction of the cleaned air) so that the output spot laser beam or spot beam reaches the center of a target area (an affected area or the like of a patient).

Further, a distance meter (a laser range finder or the like) may be disposed on the front surface of the cleaned air supply unit 5 so as to automatically measure the distance from the cleaned air supply unit 5 to a target area. When the separation distance is too large (the cleaned air supply unit 5 is too far from the target area), a warning (for example, a buzzing sound may be output or a warning lamp may be turned on or may blink) may be output to inform that the cleanliness of class 100 is not guaranteed in the range of areas visualized by the sighting unit.

The separation distance (the distance from the cleaned air supply unit 5 to the target area) in which the cleanliness of class 100 is guaranteed changes depending on the volume of the cleaned air discharged from the air discharge opening 5a. More specifically, the highly clean space is formed at a farther position as the volume increases whereas the highly clean space is limited to a closer position as the volume decreases. Thus, when a warning is output based on the value measured by the distance meter, the threshold of the separation distance for determining whether or not to output a warning is preferably set automatically according to the set volume of the cleaned air discharged from the air discharge opening 5a.

REFERENCE SIGNS LIST

1: Local cleaned air supply device
2: Base
2a: Castor
3: Power supply unit
4: Control unit
4a: Operation panel
5: Cleaned air supply unit
5a: Air discharge opening
6: Post
7, 7a to 7d: Laser emitting unit
8: Freely articulated arm
8a: Hinge
9: Control box
10: Operating table
D: Central line of flow of cleaned air
H: Horizontal axis line
L1, L2: Horizontal reference line
L3, L4: Vertical reference line
V: Vertical axis line

The invention claimed is:

1. A local cleaned air supply device comprising:
a power supply unit;
a control unit; and
a cleaned air supply unit supported so as to freely rotate, wherein:
the cleaned air supply unit includes a fan driven by driving electric power supplied from the power supply unit, a pre-filter, and a main filter, and is configured so that air drawn therein is cleaned by passing through the pre-filter and the main filter and is then discharged toward a front side of the cleaned air supply unit from an air discharge opening and so that a height position, a swing angle in a left-right direction, and a tilting angle of the cleaned air supply unit can be freely adjusted,
the cleaned air supply unit includes a sighting unit that visualizes a range in which high cleanliness is guaranteed in a space on the front side of the cleaned air supply unit, to which the cleaned air is supplied from the air discharge opening,
the sighting unit includes a plurality of laser emitting units that output laser beams toward a front side of the air discharge opening, and the laser beams are output to surround the range in which high cleanliness is guaranteed in the space in the front side of the cleaned air supply unit, and
the plurality of laser emitting units are disposed around the air discharge opening on the front side of the cleaned air supply unit.

2. The local cleaned air supply device according to claim 1, wherein the cleaned air supply unit is supported by a freely articulated arm having a plurality of hinges and is configured to freely adjust a three-dimensional position thereof.

3. The local cleaned air supply device according to claim 1, wherein the laser beams are output in parallel to a central line of the flow of the cleaned air discharged from the air discharge opening, these laser beams passing through positions separated by a predetermined distance from the central line.

4. The local cleaned air supply device according to claim 1, wherein:
an acceleration sensor is included in a casing of the cleaned air supply unit, and
when a three-dimensional position, the swing angle in the left-right direction, or the tilting angle of the cleaned air supply unit is changed, the acceleration sensor detects the change, and laser beams are automatically output for a predetermined period after the detection.

5. The local cleaned air supply device according to claim 1, wherein:
a distance meter is disposed in the cleaned air supply unit so as to automatically measure a distance from the cleaned air supply unit to a target area, and
when the distance exceeds a predetermined value, a warning is output to inform that high cleanliness is not guaranteed in the range visualized by the sighting unit.

6. The local cleaned air supply device according to claim 5, wherein a threshold of the separation distance for determining whether or not to output the warning is set automatically according to a set flow of the cleaned air discharged from the air discharge opening.

7. The local cleaned air supply device according to claim 2, wherein the laser beams are output in parallel to a central line of the flow of the cleaned air discharged from the air discharge opening, these laser beams passing through positions separated by a predetermined distance from the central line.

8. The local cleaned air supply device according to claim 2, wherein:
an acceleration sensor is included in a casing of the cleaned air supply unit, and
when a three-dimensional position, the swing angle in the left-right direction, or the tilting angle of the cleaned air supply unit is changed, the acceleration sensor detects the change, and laser beams are automatically output for a predetermined period after the detection.

9. The local cleaned air supply device according to claim 3, wherein:
an acceleration sensor is included in a casing of the cleaned air supply unit, and
when a three-dimensional position, the swing angle in the left-right direction, or the tilting angle of the cleaned air supply unit is changed, the acceleration sensor detects the change, and laser beams are automatically output for a predetermined period after the detection.

10. The local cleaned air supply device according to claim 7, wherein:
an acceleration sensor is included in a casing of the cleaned air supply unit, and
when a three-dimensional position, the swing angle in the left-right direction, or the tilting angle of the cleaned air supply unit is changed, the acceleration sensor detects the change, and laser beams are automatically output for a predetermined period after the detection.

11. The local cleaned air supply device according to claim 2, wherein:
a distance meter is disposed in the cleaned air supply unit so as to automatically measure a distance from the cleaned air supply unit to a target area, and
when the distance exceeds a predetermined value, a warning is output to inform that high cleanliness is not guaranteed in the range visualized by the sighting unit.

12. The local cleaned air supply device according to claim 3, wherein:
a distance meter is disposed in the cleaned air supply unit so as to automatically measure a distance from the cleaned air supply unit to a target area, and
when the distance exceeds a predetermined value, a warning is output to inform that high cleanliness is not guaranteed in the range visualized by the sighting unit.

13. The local cleaned air supply device according to claim 4, wherein:
a distance meter is disposed in the cleaned air supply unit so as to automatically measure a distance from the cleaned air supply unit to a target area, and
when the distance exceeds a predetermined value, a warning is output to inform that high cleanliness is not guaranteed in the range visualized by the sighting unit.

14. The local cleaned air supply device according to claim 7, wherein:
a distance meter is disposed in the cleaned air supply unit so as to automatically measure a distance from the cleaned air supply unit to a target area, and
when the distance exceeds a predetermined value, a warning is output to inform that high cleanliness is not guaranteed in the range visualized by the sighting unit.

15. The local cleaned air supply device according to claim 8, wherein:
a distance meter is disposed in the cleaned air supply unit so as to automatically measure a distance from the cleaned air supply unit to a target area, and when the distance exceeds a predetermined value, a warning is output to inform that high cleanliness is not guaranteed in the range visualized by the sighting unit.

16. The local cleaned air supply device according to claim 9, wherein:
    a distance meter is disposed in the cleaned air supply unit so as to automatically measure a distance from the cleaned air supply unit to a target area, and
    when the distance exceeds a predetermined value, a warning is output to inform that high cleanliness is not guaranteed in the range visualized by the sighting unit.

17. The local cleaned air supply device according to claim 10, wherein:
    a distance meter is disposed in the cleaned air supply unit so as to automatically measure a distance from the cleaned air supply unit to a target area, and
    when the distance exceeds a predetermined value, a warning is output to inform that high cleanliness is not guaranteed in the range visualized by the sighting unit.

18. The local cleaned air supply device according to claim 1, wherein the plurality of laser emitting units are disposed at an upper side, a lower side, a left side, and a right side of the air discharge opening on the front side of the cleaned air supply unit.

19. The local cleaned air supply device according to claim 1, wherein:
    the laser emitting units disposed on the upper side and the lower side of the air discharge opening emit horizontal laser beams,
    the laser emitting units disposed at the left side and the right side of the air discharge opening emit vertical laser beams, and
    the horizontal and vertical laser beams respectively form horizontal and vertical reference lines to surround the range in which high cleanliness is guaranteed in the space in the front side of the cleaned air supply unit.

* * * * *